(12) United States Patent
Dubuclet et al.

(10) Patent No.: US 10,420,930 B2
(45) Date of Patent: Sep. 24, 2019

(54) PADDLE LEAD WITH ELASTIC DEFLECTION COUPLING BETWEEN FEED WIRE AND PADDLE

(71) Applicant: PACESETTER, INC., Sylmar, CA (US)

(72) Inventors: Jodi Townsley Dubuclet, Dallas, TX (US); Jeffrey Urbanski, Frisco, TX (US)

(73) Assignee: PACESETTER, INC., Sylmar, CA (US)

( * ) Notice: Subject to any disclaimer, the term of this patent is extended or adjusted under 35 U.S.C. 154(b) by 3 days.

(21) Appl. No.: 15/431,519

(22) Filed: Feb. 13, 2017

(65) Prior Publication Data

US 2018/0229030 A1   Aug. 16, 2018

(51) Int. Cl.
*A61N 1/05* (2006.01)
*A61N 1/04* (2006.01)

(52) U.S. Cl.
CPC ........... *A61N 1/0553* (2013.01); *A61N 1/048* (2013.01); *A61N 1/05* (2013.01)

(58) Field of Classification Search
CPC ......... A61N 1/0553; A61N 1/05; A61N 1/048
See application file for complete search history.

(56) References Cited

U.S. PATENT DOCUMENTS

| 4,287,896 A * | 9/1981 | Grigorov | A61N 1/056 607/122 |
| 2015/0018910 A1 * | 1/2015 | Chen | A61N 1/05 607/116 |
| 2016/0250466 A1 * | 9/2016 | Boggs, II | A61N 1/36021 607/46 |
| 2018/0221646 A1 * | 8/2018 | Silverton | A61N 1/048 |

* cited by examiner

*Primary Examiner* — Tammie K Marlen (57) ABSTRACT

An implantable medical lead may include a lead body, a substrate, and an elastic deflection component. The lead body includes a proximal end configured to couple to an implantable pulse generator, a distal end opposite the proximal end, and an electrical conductor extending through the lead body. The substrate is at the distal end and supports an array of electrodes. The elastic deflection component physically and electrically connects the electrical conductor and an electrode of the array of electrodes. The elastic deflection component is configured to compensate for at least one of tension forces or compression forces transferred from the electrical conductor to the electrode of the array of electrodes.

20 Claims, 7 Drawing Sheets

PADDLE LEAD WITH ELASTIC DEFLECTION COUPLING BETWEEN FEED WIRE AND PADDLE

TECHNICAL FIELD

Aspects of the present disclosure relate to leads surgically implantable in a patient for electrical stimulation of nerve or tissue. More particularly, the present disclosure pertains to improvements to such implantable medical leads that reduce the likelihood of lead displacement and lead damage.

BACKGROUND

Medical conditions may be treated through the application of electrical stimulation to patient tissue targeted for treatment. For example, implantable pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems, are commonly linked to targeted patient tissue via one or more implantable medical leads. As a result, electrical stimulation originating in the IPG is transmitted to the targeted patient tissue via the one or more implantable medical leads. Conversely and where applicable for the type of therapy, the one or more implantable medical leads transmit electrical signals originating in the targeted patient tissue to the IPG to be sensed by the IPG.

Various lead configurations may be used to deliver electrical stimulation to cardiac tissue to treat cardiac conditions such as, for example, bradycardia, tachycardia, etc. In doing so, the distal region of the implantable medical lead, which supports one or more electrodes, is attached to the targeted patient tissue, which is typically cardiac tissue that is moving on account of the patient heart beating. This tissue displacement can result in dislodgement of the attached distal region of the implantable medical lead and/or damage to the implantable medical lead.

Spinal Cord Stimulation (SCS) is a type of chronic pain management that involves driving an electrical current into particular regions of the spinal cord to induce paresthesia, which is a subjective sensation of numbness or tingling in a region of the body associated with the stimulated spinal cord region. Paresthesia masks the transmission of chronic pain sensations from the afflicted regions of the body to the brain, thereby providing pain relief to the patient.

Typically, an SCS system delivers electrical current through electrodes implanted along the dura layer surrounding the spinal cord. The electrodes may be carried, for example, by a paddle lead, which has at its distal region a paddle-like configuration with the electrodes arranged on a relatively large planar surface area, or a percutaneous lead, which also includes the electrodes at its distal region, but the electrodes are arranged around a tube.

The spine is capable of significant displacement when transitioning from extension to flexion and vice versa. The tissue displacement associated with spinal extension/flexion can result in dislodgement and/or damage to a distal region of an implantable medical lead implanted in the area of extension/flexion.

It is with these observations in mind, among others, that various aspects of the present disclosure were conceived and developed.

SUMMARY

Implementations described and claimed herein address the foregoing problems, among others, by providing an implantable medical lead with an elastic deflection component between a lead body conductor and an electrode at a distal end of the lead. The elastic deflection component electrically connects the conductor to the electrode and reduces the extent to which tension/compression forces are transferred from the conductor to the electrode, thereby reducing the chance of lead failure or migration due to spinal flexion/extension.

In one embodiment, the implantable medical lead includes a paddle, a lead body and a spring. The paddle supports an electrode. The lead body extends proximally from the paddle and includes an electrical conductor extending through the lead body. The spring physically and electrically connects the electrical conductor to the electrode.

The spring may include a helical spring. The helical spring may include an end region that is more tightly coiled than an intermediate region of the helical spring.

An electrically insulating polymer jacket may extend about the spring. The spring may be welded to at least one of the conductor or the electrode. Alternatively or additionally, the spring may be crimped to at least one of the conductor or the electrode.

In one embodiment, the implantable medical lead may include a lead body, a substrate, and an elastic deflection component. The lead body includes a proximal end configured to couple to an implantable pulse generator, a distal end opposite the proximal end, and an electrical conductor extending through the lead body. The substrate is at the distal end and supports an array of electrodes. The elastic deflection component physically and electrically connects the electrical conductor and an electrode of the array of electrodes. The elastic deflection component is configured to compensate for at least one of tension forces or compression forces transferred from the electrical conductor to the electrode of the array of electrodes.

The elastic deflection component may include a spring. The spring may include a helical spring. The helical spring may include an end region that is more tightly coiled than an intermediate region of the helical spring. An electrically insulating polymer jacket may extend about an outer circumferential surface of the helical spring.

The elastic deflection component may be welded to at least one of the conductors or the electrode of the array of electrodes. Alternatively or additionally, the elastic deflection component may be crimped to at least one of the conductors or the electrode of the array of electrodes.

The substrate may include a paddle. In such an instance, the implantable medical lead will be a paddle lead.

The deflection component may be configured to elongate under a tensile load of less than approximately 1.1 pounds to a length sufficient to accommodate cervical extension/flexion without damage to the implantable medical lead.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

DETAILED DESCRIPTION

Aspects of the present disclosure involve implantable medical leads, and in some specific instances, paddle leads. The implantable medical leads include an elastic deflection component that is electrically conductive. The elastic deflection component physically and electrically connects a lead body conductor to an electrode at a distal end of the implantable medical lead. The elastic deflection component reduces the extent to which tension/compression forces are transferred from the conductor to the electrode, thereby reducing the likelihood of lead failure or migration due to spinal flexion/extension.

Figure 1:
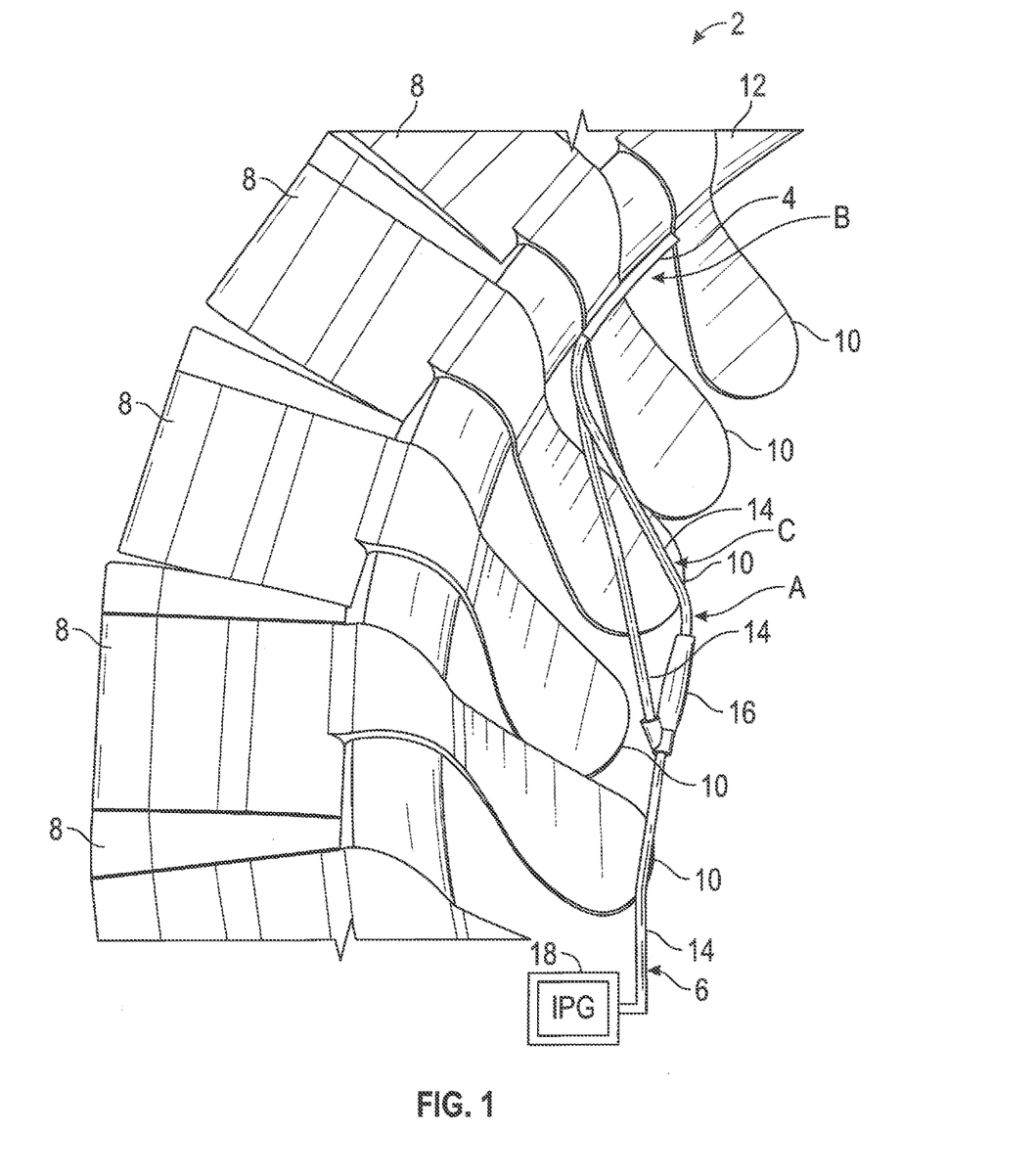
FIG. 1 is diagrammatic sagittal view of a portion of a patient spine in extension and having a distal end of an implantable medical lead implanted on the spine.
Figure 2:
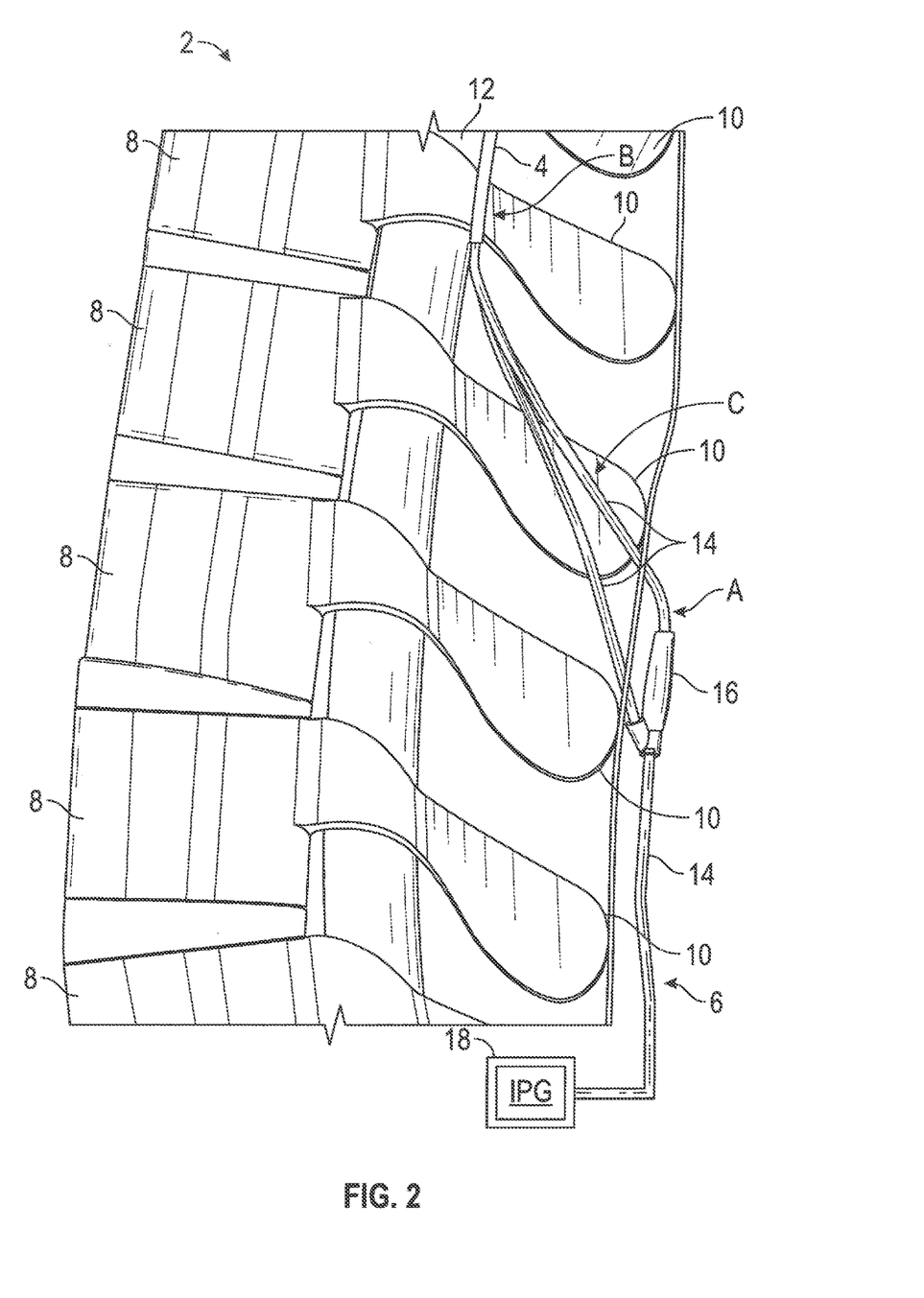
FIG. 2 is the same view as FIG. 1, except the patient spine is in flexion.

FIGS. 1 and 2 are diagrammatic sagittal views of a portion of a patient spine 2 with a distal end 4 of an implantable medical lead 6 implanted on the spine 2. As respectively reflected in FIGS. 1 and 2, the spine 2 is capable of extension and flexion. When the spine 2 is in extension, it tilts posteriorly. Each vertebral body 8 of the patient spine 2 includes a posteriorly extending spinous process 10, and the spinous processes 10 of the patient spine 2 converge towards each other as the spine extends, the patient spine arching posteriorly as a result. Conversely, when the spine 2 is in flexion, it tilts anteriorly, and the spinous processes 10 of the patient spine 2 diverge away from each other, the patient spine bending anteriorly as a result.

As can be understood from FIGS. 1 and 2, the distal end 4 of the lead 6, which may be in the form of a paddle 4 of a paddle lead 6, is implanted adjacent nerve tissue 12. The body 14 of the lead 6 extends posteriorly from the paddle 4 to an anchor 16 on or near a posterior edge of a spinous process 10 before extending inferiorly to connect to the IPG 18 that administers the electrotherapy via the lead 6 and is implanted elsewhere in the patient body.

The lead body 14 is essentially fixed to the patient at points A and B in FIGS. 1 and 2 on account of the fixation of the paddle 4 and the anchor 16. Thus, the segment of the lead body 14 in the region called out by arrow C is placed in compression when the spine 2 is in extension (FIG. 1) and placed in tension when the spine 2 is in flexion (FIG. 2). Thus, absent the below described elastic deflection component 19 of the lead, the repeated tension/compression cycle may result in lead failure and/or displacement of the paddle 4 relative to the target tissue.

Figure 3:
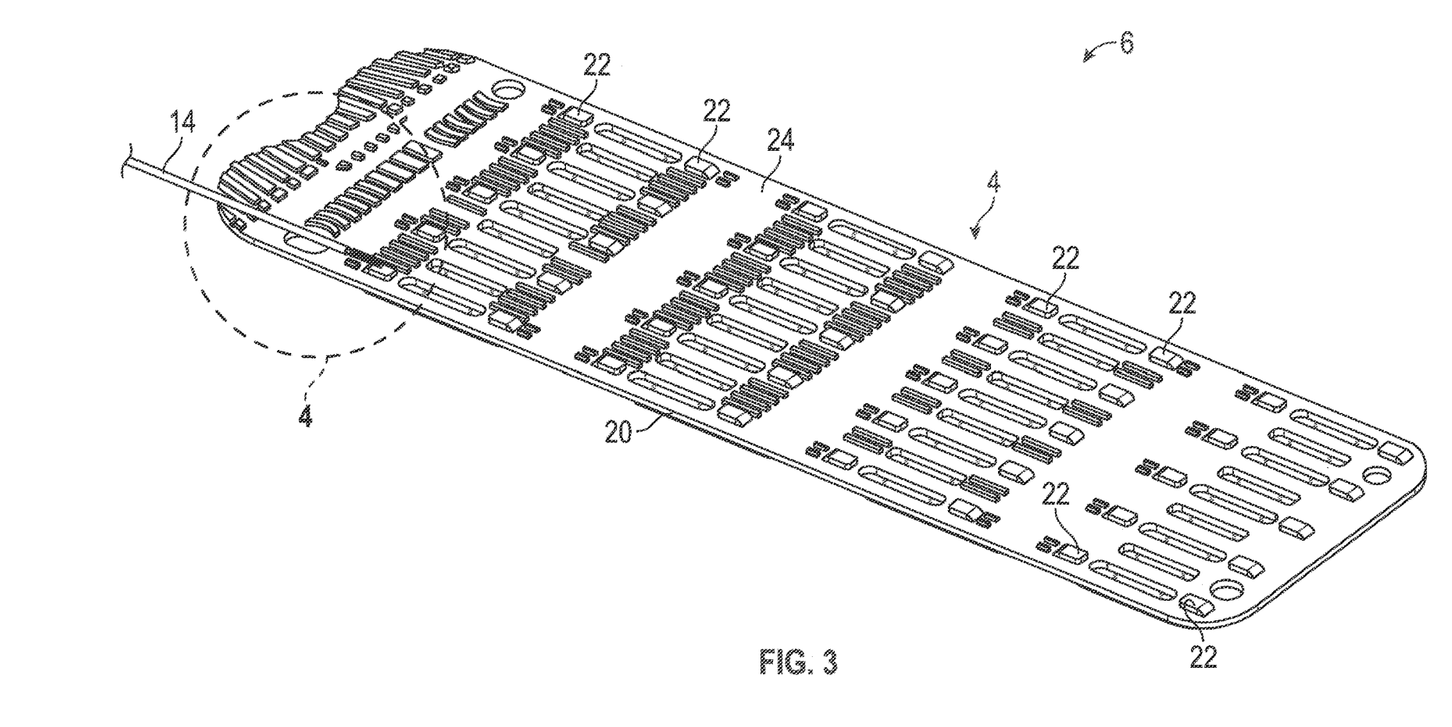
FIG. 3 is an isometric view of a distal region of the lead depicted in FIGS. 1 and 2.

As illustrated in FIG. 3, which is an isometric view of a distal region of the lead 6 depicted in FIGS. 1 and 2, the lead 6 may include a paddle 4 and a lead body 14 extending proximally from the paddle 4. The paddle 4 may be in the form of a planar thin body or substrate 20 having a width and length that is substantially greater than its thickness. The paddle 4 may include a number of electrodes 22 on one of the planar surfaces 24 of the substrate 20. The electrodes 20 may be arranged in a variety of arrangements, including a series of linear rows and columns as depicted in FIG. 3.

Figure 4:
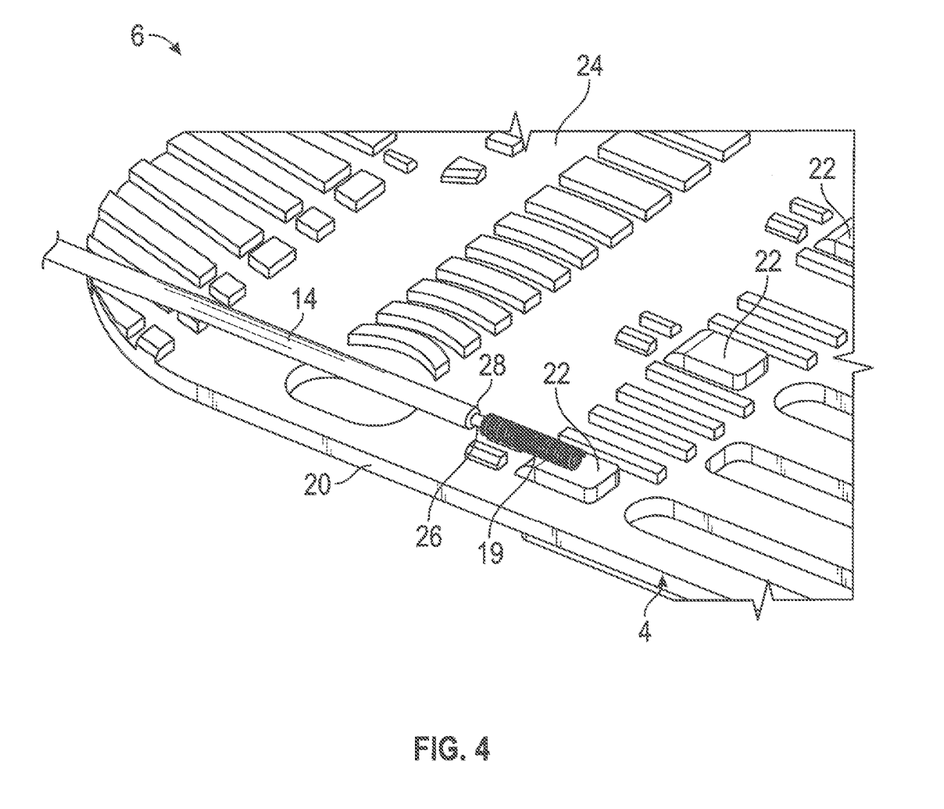
FIG. 4 is an enlarged view of a portion of the lead encircled in FIG. 3.

As depicted in FIG. 4, which is an enlarged view of a portion of the lead 6 encircled in FIG. 3, the lead body 14 may include an inner electrical conductor 26 and an outer electrical insulation jacket 28 that surrounds and encases the conductor 26. The conductor 26 may be in the form of a solid core wire or a multi-filar conductor, either of which may be made of an electrically conductive and biocompatible metal commonly employed in the industry. The jacket 28 may be formed of a polymer or other electrical insulating material commonly employed in the industry.

As shown in FIG. 4, an elastic deflection component 19 of the lead 6 extends from a distal end of the conductor 26 of the lead body 14 to an electrode 22 of the paddle 4. As will be discussed in greater detail below, the respective ends of the elastic deflection component 19 may be coupled to the conductor 26 and electrode 22 via a variety of arrangements, including, for example, welding, crimping, and/or etc. The elastic deflection component 19 is resilient and configured to repeatedly elongate and compress along its length and between its respective attachments to the conductor and electrode. As a result, the deflection component 19 allows the patient spine to extend/flex as illustrated in FIGS. 1 and 2 without causing a failure in the attachment of the conductor to the electrode. In other words, the deflection component 19 can be considered a tension/compression compensation component 19 because it can mitigate the extent to which tension and compression forces impact the physical connection between the conductor and electrode, such physical connection typically being in the form of a weld and/or crimp. The deflection component 19 also reduces the likelihood that spine extension/flexion will cause the paddle 4 to migrate.

On account of the deflection component 19 and as compared to paddles known in the art, the paddle 4 has increased flexibility (or conformability) and improved robustness via a reduced mechanical failure rate. Due to its increased flexibility (or conformability), the paddle 4 disclosed herein can take form based on each patient's anatomical curvature in the spine. This ability to take form allows the paddle 4 to accommodate a variety of spinal cord and spinal canal diameter ranges, as well as a wide range of anatomical anomalies such as bone spurs, calcium growths or etc. The ability to take form also helps to accommodate body motion without lead damage or migration.

It should be noted, that while FIGS. 3 and 4 depict the lead 6 as having a single lead body 14 with a single conductor 26 extending to, and coupling with via an elastic deflection component 19, a single electrode 22 of the multi-electrode paddle 4, such an embodiment is merely provided as one non-limiting example. In other embodiments, the lead 6 may have a single lead body 14 with multiple individual conductors 26 respectively extending to individual electrodes 22 of the multi-electrode paddle 4, the coupling of a conductor to a respective electrode including at least one elastic deflection component 19. Similarly, in other embodiments, the lead 6 may have a multiple lead bodies 14 or branches of the lead body respectively extending to individual electrodes 22 of the multi-electrode paddle 4, each lead body or branch of the lead body having a conductor 26 that couples to a respective electrode 22, each respective coupling of a conductor to an electrode occurring via at least one elastic deflection component 19.

Figure 5:
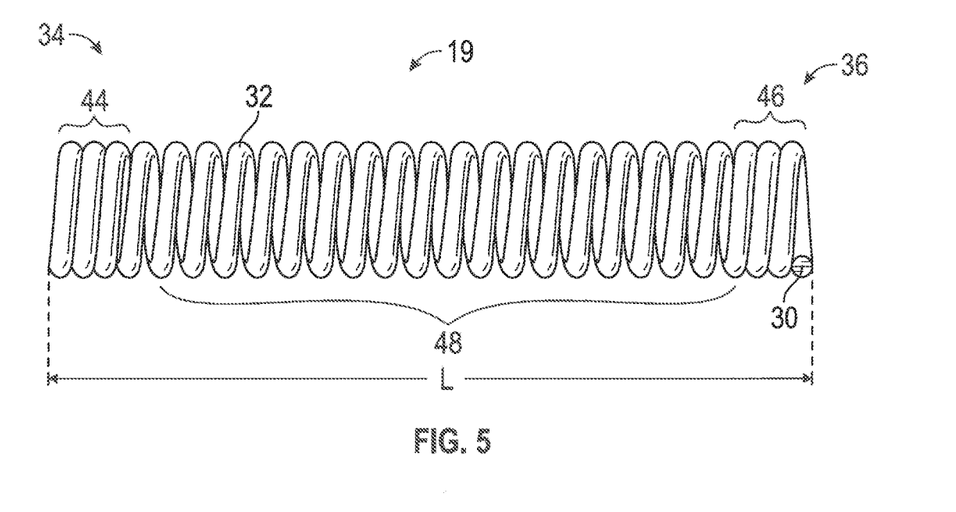
FIG. 5 is a longitudinal side view of an exemplary deflection component in the form of a helical winding, spring or coil.
Figure 6:
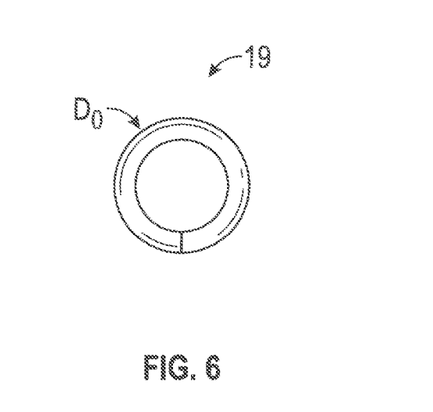
FIG. 6 is an end view of an exemplary deflection component depicted in FIG. 5.

FIGS. 5 and 6 are, respectively, a longitudinal side view and an end view of an exemplary deflection component 19 in the form of a helical winding, spring or coil 19. As shown in FIG. 5, the helical coil 19, which may be a helical micro-spring, includes a wire 30 helically wound into a plurality of adjacent coil loops or turns 32. The helical coil 19 also includes a distal end 34 and a proximal end 36. In one embodiment, the helical coil 19 may be relatively short with a length L of approximately 0.037 inch to approximately 0.079 inch between the ends 34, 36, the length L being long enough to accommodate being between two vertebral segments. Alternatively, in one embodiment, the helical coil 19 may be substantially longer with a length L of approximately 1.18 inch to approximately 1.58 inch between the ends 34, 36, the length L being long enough to be routed from the proximal end of the paddle to the most distal electrode of the paddle.

The helical coil may have an outer diameter Do of approximately 0.0065 inch, plus or minus 0.0005 inch. The wire 30 may have a diameter of approximately 0.001 inch, plus or minus 0.0002 inch and be formed of biocompatible electrically conductive metals such as, for example, MPN35, stainless steel, etc.

In one embodiment, the helical coil 19 of FIGS. 5 and 6 may have a constant coil pitch from end 34 to end 36 of approximately 0.001 to approximately 0.004. The wider or more open the coil pitch of the helical coil 19, the greater the ability of the helical coil 19 to accommodate compression, in addition to tension.

Alternatively, and as depicted in FIG. 5, the helical coil 19 may have a variable coil pitch along its length such that a distal region 44 and a proximal region 46 are tightly or more closely coiled at a coil pitch of approximately 0.001 to approximately 0.004, and an intermediate region 48 between the two end regions 44, 46 is less tightly or more openly coiled at a coil pitch of approximately 0.004 to approximately 0.008. The wider or more open the coil pitch of the intermediate region 48, the greater the ability of the helical coil 19 to accommodate compression, in addition to tension. The tighter or more closed coil pitch at the distal and proximal regions 44, 46 creates a tube feature to receive therein the conductor 26 and also improved ability to be welded, both of these benefits increasing as the coil pitch becomes tighter.

In one embodiment, as illustrated in FIG. 5, the three most distal and three most proximal coil turns 32 will be closed-wound, while the coil turns 32 of the intermediate region 48 will be open-wound. There may be approximately 25 coil turns 35 end-to-end of the helical coil 19.

Figure 7:
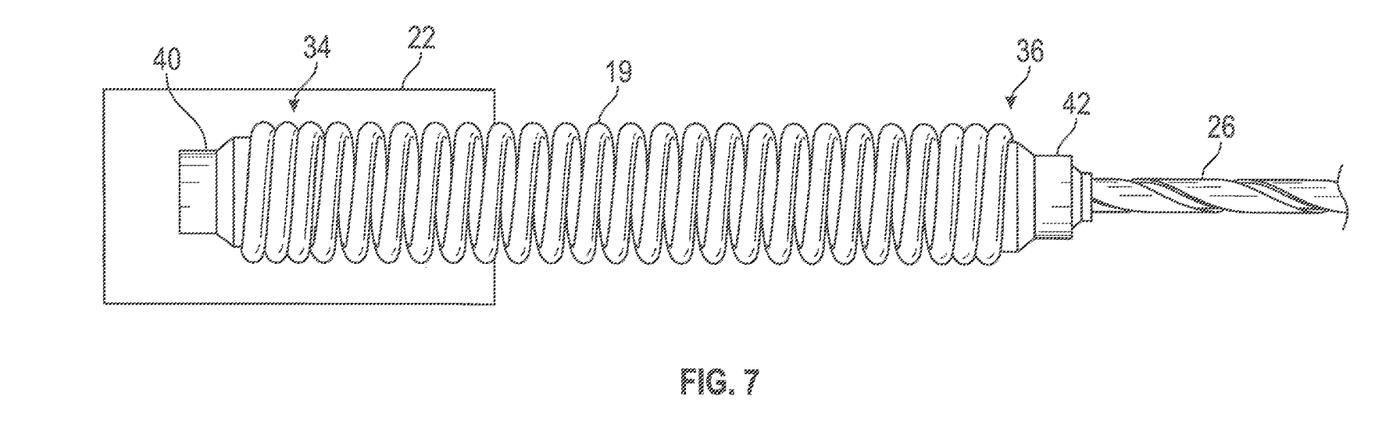
FIG. 7 is a plan view of the helical coil of FIGS. 5 and 6 welded to the electrode and conductor of the lead of FIG. 4.

FIG. 7 is a plan view of the helical coil 19 of FIGS. 5 and 6. As shown in FIG. 7, the distal end 34 of the helical coil 19 is welded via a distal weld 40 to the electrode 22 of the paddle 4 depicted in FIG. 4. Similarly, the proximal end 36 of the helical coil 19 is welded via a proximal weld 42 to the conductor 26 of the lead body 14 depicted in FIG. 4. The welding may take place via laser or resistance welding.

As can be understood from FIGS. 4 and 7, the deflection component 19 is designed to reduce tensile loads translated through the lead body 14 to the weld 40 of the deflection component 19 with the electrode 22. In one embodiment, the ultimate tensile strength of the lead body 14 is approximately 1.1 pounds. In such an embodiment, the deflection component 19 is designed to elongate under a tensile load of less than 1.1 pounds to a length sufficient to accommodate cervical extension/flexion, which is considered the worst type of spinal extension/flexion.

Figure 8:
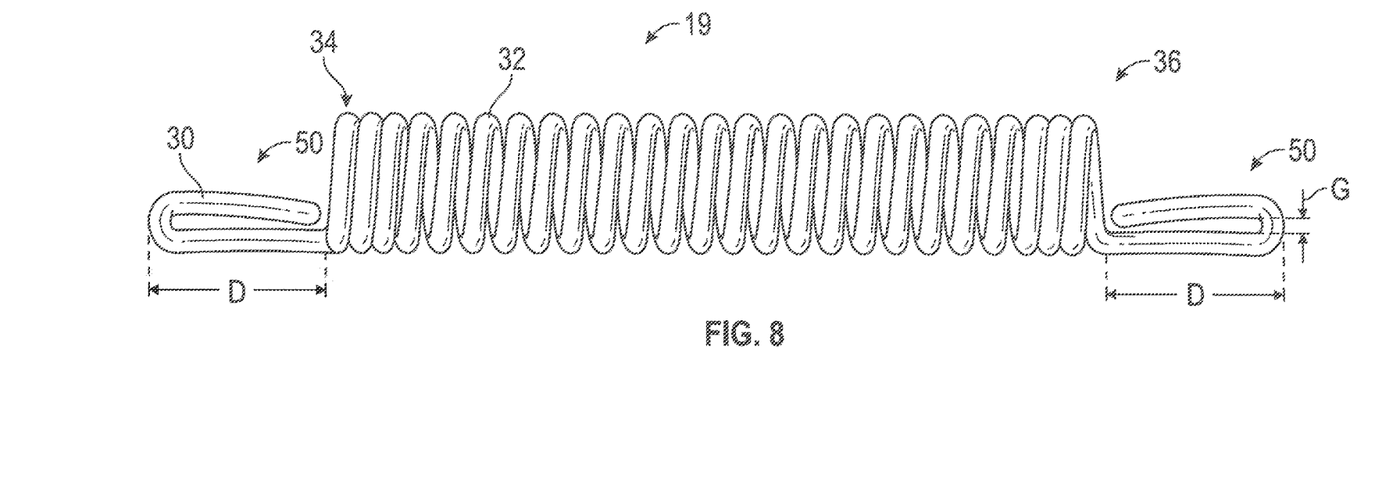
FIG. 8 is a longitudinal side view of a helical winding, spring or coil with wire terminations that are in the form of pigtailed crimp features.

As shown in FIG. 8, which is a longitudinal side view of a helical winding, spring or coil 19, in some instances the wire 30 of the helical coil 19 will terminate at the distal and proximal ends 34, 36 in the form of a pigtailed crimp feature 50 wherein the wire 30 is bent back upon itself. Each crimp feature 50 may extend from its respective coil end 34, 36 by a distance D of approximately 0.02 inch, plus or minus 0.01 inch. Each crimp feature 50 may have a gap G between the parallel segments of the crimp feature of approximately 0.0035 inch, plus or minus 0.001 inch. The crimp features 50 may be employed in manufacturing the lead 6 by providing a grasping feature 50 whereby the wire 30 can be pulled through a tight fit and then resistance welded to the electrode 22.

Figure 9:
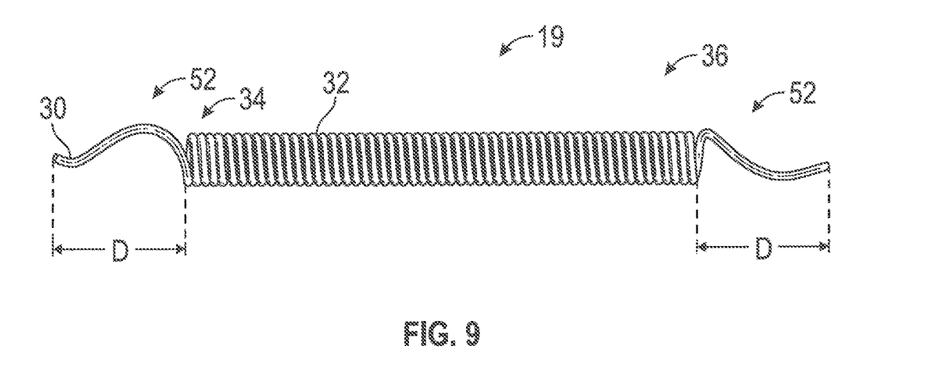
FIG. 9 is a longitudinal side view of a helical winding, spring or coil with straightened or elongated wire terminations.

As shown in FIG. 9, which is a longitudinal side view of a helical winding, spring or coil 19, in some instances the wire 30 of the helical coil 19 will terminate at the distal and proximal ends 34, 36 as straightened or elongated wire terminations 52. Each straightened or elongated wire termination 52 may extend from its respective coil end 34, 36 by a distance D of approximately 0.004 inch, plus or minus 0.001 inch. The straightened or elongated wire termination 52 may be employed in manufacturing the lead 6 by providing a region whereby the wire 30 can be resistance welded at its respective ends to the electrode 22 and the conductor 26. The straightened or elongated wire terminations 52 can end blunt, or be formed around a peg to create a loop.

Figure 10:
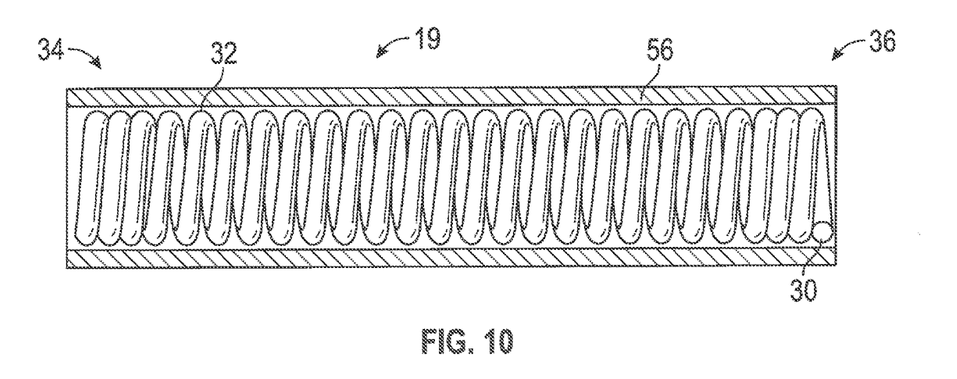
FIG. 10 is a longitudinal side view of an exemplary deflection component in the form of a helical winding, spring or coil, wherein the deflection component further includes an insulation component and the insulation component is shown in cross-section to reveal the deflection component contained therein.

FIG. 10 is a longitudinal side view of an exemplary deflection component in the form of a helical winding, spring or coil, wherein the deflection component further includes an insulation component 56 and the insulation component 56 is shown in cross-section to reveal the deflection component contained therein. As shown in FIG. 10, an insulating sleeve or tube 56 can be used to cover the helical coil 19, thereby preventing silicone from getting into the helical coil 19 during the overmolding part of the lead manufacturing process. The tube 56 may be made of polytetrafluoroethylene ("PTFE") or other biocompatible polymer materials.

In one embodiment, the helical coil 19 may be purposely allowed to be impregnated with silicone prior to or during the overmolding part of the lead manufacturing process. The silicone impregnation may facilitate improved performance of the helical coil 19 with respect to relieving stresses inflicted on the weld joint between the distal end of the helical coil and the electrode of the paddle.

Figure 11:
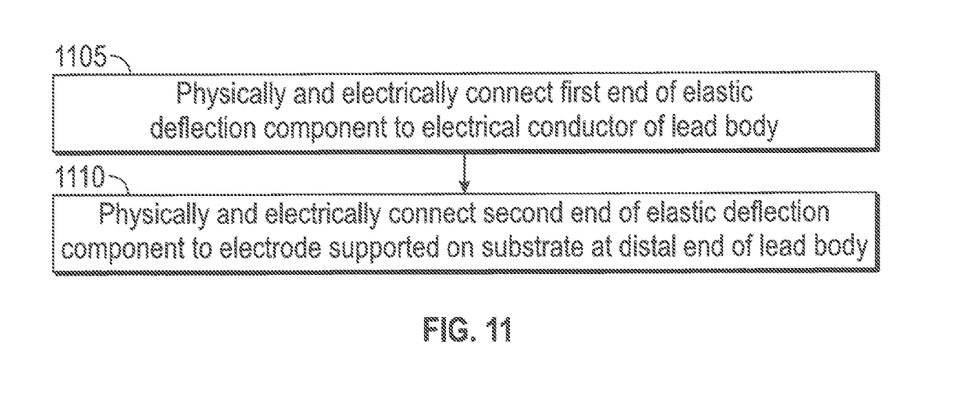
FIG. 11 is a flow chart outlining an example methodology for manufacturing certain aspects of the implantable medical lead disclosed herein.

FIG. 11 is a flow chart outlining an example methodology for manufacturing the above-described aspects of the implantable medical lead. As illustrated in FIG. 11, a first end of an elastic deflection component is physically and electrically connected to an electrical conductor of a lead body [block 1105]. A second end of the elastic deflection component is physically and electrically connected to an electrode supported on a substrate at a distal end of the lead body [block 1110]. Of course, these steps could be reversed.

In one version of the method, the physical and electrical connections occur via at least one of welding or crimping. Also, in one version of the method, the elastic deflection component includes a spring, which may even be a helical spring. Also, a biocompatible polymer sheath may be provided about the spring.

While the above discussion takes place mainly in the context of the paddle leads, the concepts disclosed herein are readily applicable to other types of leads wherein the substrate supporting the electrode(s) is tubular or of other shapes and configurations. Also, while the above discussion takes place mainly in the context of the elastic deflection component being a helical spring 19, the concepts disclosed herein are readily applicable to other types of electrically conductive spring configurations or other resilient biasing members known in the art. For example, the spring 19 can have shapes that are sinusoidal, infinity, omega, saw tooth, or be springs with varied spring loop diameters, etc. Also, depending on the embodiment, the lead conductors 26 may be configured as springs and substituted for the separate or additional elastic deflection component depicted in the FIG. 4 as a helical spring 19. Such an embodiment would be advantageous in that it would eliminate the extra mechanical connection from the conductor 26 to the spring 19.

Various other modifications and additions can be made to the exemplary implementations discussed without departing from the spirit and scope of the presently disclosed technology. For example, while the embodiments described above refer to particular features, the scope of this disclosure also includes implementations having different combinations of features and implementations that do not include all of the described features. Accordingly, the scope of the presently disclosed technology is intended to embrace all such alternatives, modifications, and variations together with all equivalents thereof.

What is claimed is:

1. An implantable medical lead comprising:
   a paddle comprising a substrate and a plurality of electrodes arranged on the substrate in an array;
   a lead body extending proximally from the paddle and including an electrical conductor extending through the lead body; and
   a spring physically and electrically connecting the electrical conductor to an electrode of the plurality of electrodes arranged on the substrate.

2. The implantable medical lead of claim 1, wherein the spring includes a helical spring, and wherein the substrate is a planar thin body.

3. The implantable medical lead of claim 2, wherein the helical spring includes an end region that is more tightly coiled than an intermediate region of the helical spring.

4. The implantable medical lead of claim 1, further comprising an electrically insulating polymer jacket extending about the spring.

5. The implantable medical lead of claim 1, wherein the spring is welded to at least one of the conductor or the electrode.

6. The implantable medical lead of claim 1, wherein the spring is crimped to at least one of the conductor or the electrode.

7. An implantable medical lead comprising:
   a lead body including a proximal end configured to couple to an implantable pulse generator, a distal end opposite the proximal end, and an electrical conductor extending through the lead body;
   a substrate at the distal end, the substrate supporting a plurality of electrodes arranged in an array of on the substrate; and
   an elastic deflection component physically and electrically connecting the electrical conductor and an electrode of the plurality of electrodes arranged on the substrate, the elastic deflection component configured to compensate for at least one of tension forces or compression forces transferred from the electrical conductor to the electrode of the array of electrodes.

8. The implantable medical lead of claim 7, wherein the elastic deflection component includes a spring.

9. The implantable medical lead of claim 8, wherein the spring includes a helical spring.

10. The implantable medical lead of claim 9, wherein the helical spring includes an end region that is more tightly coiled than an intermediate region of the helical spring.

11. The implantable medical lead of claim 9, further comprising an electrically insulating polymer jacket extending about an outer circumferential surface of the helical spring.

12. The implantable medical lead of claim 7, wherein the elastic deflection component is welded to at least one of the conductor or the electrode of the array of electrodes.

13. The implantable medical lead of claim 7, wherein the elastic deflection component is crimped to at least one of the conductor or the electrode of the array of electrodes.

14. The implantable medical lead of claim 7, wherein the substrate is a planar thin body.

15. The implantable medical lead of claim 7, wherein the deflection component is configured to elongate under a tensile load of less than approximately IA pounds to a length sufficient to accommodate cervical extension/flexion without damage to the implantable medical lead.

16. An implantable medical lead comprising:
   a lead body including a proximal end configured to couple to an implantable pulse generator, a distal end opposite the proximal end;
   a plurality of electrical conductors extending through the lead body;
   a substrate at the distal end, the substrate supporting a plurality of electrodes arranged in an array on the substrate; and
   a plurality of elastic deflection components physically and electrically connecting each of the plurality of electrical conductors and with a corresponding electrode of the plurality of electrodes arranged on the substrate, with each of the plurality of elastic deflection components configured to compensate for at least one of tension forces or compression forces transferred from the electrical conductors to the array of electrodes.

17. The implantable medical lead of claim 16, wherein at least one of the plurality of elastic deflection components includes a spring.

18. The implantable medical lead of claim 17, wherein the spring includes a helical spring, and wherein the substrate is a planar thin body.

19. The implantable medical lead of claim 18, wherein the helical spring includes an end region that is more tightly coiled than an intermediate region of the helical spring.

20. The implantable medical lead of claim 16, wherein at least one of the plurality of elastic deflection components is welded to at least one of the conductor or the electrode of the array of electrodes.

* * * * *